US010046107B2

(12) United States Patent
Zitting et al.

(10) Patent No.: US 10,046,107 B2
(45) Date of Patent: *Aug. 14, 2018

(54) STORABLE INTRAVENOUS STANDS

(71) Applicant: Maxtec, LLC, Salt Lake City, UT (US)

(72) Inventors: Darryl Zitting, Salt Lake City, UT (US); Jeffrey Valjean Anderson, Salt Lake City, UT (US); Carl Ross Wecker, Salt Lake City, UT (US)

(73) Assignee: MAXTEC, LLC, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/979,762

(22) Filed: Dec. 28, 2015

(65) Prior Publication Data
US 2016/0184508 A1    Jun. 30, 2016

Related U.S. Application Data

(60) Continuation of application No. 14/187,943, filed on Feb. 24, 2014, now Pat. No. 9,227,007, which is a
(Continued)

(51) Int. Cl.
*F16M 11/42* (2006.01)
*F16M 11/20* (2006.01)
(Continued)

(52) U.S. Cl.
CPC ............ *A61M 5/1415* (2013.01); *B62B 3/006* (2013.01); *B62B 3/18* (2013.01); *F16M 11/42* (2013.01);
(Continued)

(58) Field of Classification Search
CPC ...... B01L 9/00; A61M 5/1415; G03B 17/561; B62B 3/14; B62B 3/1496; B62B 3/006; B62B 3/18; F16M 11/42; F16M 2200/08; Y10T 16/184
USPC ..... 248/121, 125.1, 188, 7, 127, 129, 145.6, 248/176.1, 188.7; 211/126.1, 126.7, 194, 211/126.12, 126.2, 126.3; 280/33.997, 280/79.3, 33.991, 333.995, 33.998, 651, 280/47.35, 304.1
See application file for complete search history.

(56) References Cited

U.S. PATENT DOCUMENTS

| | | | | |
|---|---|---|---|---|
| 1,893,799 | A | * | 1/1933 | Harrincton ................ B01L 9/00 248/188.7 |
| 2,170,006 | A | * | 8/1939 | Brandt ................ G03B 17/561 248/188.7 |

(Continued)

FOREIGN PATENT DOCUMENTS

| | | |
|---|---|---|
| DE | 67 50 494 U | 1/1969 |
| DE | 40 20 434 | 1/1991 |

(Continued)

*Primary Examiner* — Tan Le
(74) *Attorney, Agent, or Firm* — Schroeder Intellectual Property Law Group, LLC

(57) ABSTRACT

The present invention is directed to a base member for a portable intravenous stand. The base member includes a plurality of segments configured to facilitate the close nesting or alignment of multiple portable intravenous stands; and thus reducing the amount of space required for storing the portable intravenous stands when not in use.

14 Claims, 19 Drawing Sheets

Related U.S. Application Data division of application No. 13/469,863, filed on May 11, 2012, now Pat. No. 8,657,241, which is a division of application No. 12/287,535, filed on Oct. 10, 2008, now Pat. No. 8,196,874.

(60) Provisional application No. 60/998,863, filed on Oct. 12, 2007.

(51) Int. Cl.
*A61H 3/00* (2006.01)
*A61M 5/14* (2006.01)
*B62B 3/14* (2006.01)
*B62B 3/18* (2006.01)
*A47B 43/00* (2006.01)
*B62B 3/00* (2006.01)

(52) U.S. Cl.
CPC ........ *F16M 2200/08* (2013.01); *Y10T 16/184* (2015.01)

(56) References Cited

U.S. PATENT DOCUMENTS

| | | | |
|---|---|---|---|
| 3,026,079 A | 3/1962 | Stack | |
| 3,272,528 A | 9/1966 | Young et al. | |
| 3,303,938 A | 2/1967 | Solomon | |
| 3,888,442 A | 6/1975 | Comeaux | |
| 3,889,910 A | 6/1975 | Walters | |
| 4,054,209 A | 10/1977 | Solomon | |
| 4,332,378 A | 6/1982 | Pryor | |
| 4,456,273 A | 6/1984 | McKinnon | |
| 4,541,596 A | 9/1985 | Price | |
| 4,744,536 A | 5/1988 | Bancalari | |
| 4,911,308 A | 3/1990 | Nylund | |
| D310,570 S | 9/1990 | Wells | |
| 5,048,789 A | 9/1991 | Eason et al. | |
| 5,125,520 A | 6/1992 | Kawasaki | |
| 5,344,169 A | 9/1994 | Pryor et al. | |
| 5,458,305 A * | 10/1995 | Woodward .......... | A61M 5/1415 248/121 |
| 5,479,953 A | 1/1996 | Pasulka | |
| 5,501,419 A | 3/1996 | Huang | |
| 5,556,065 A | 9/1996 | Wadley | |
| 5,957,309 A | 9/1999 | Hall | |
| 6,158,701 A * | 12/2000 | Deshler .............. | B05B 13/0285 248/125.1 |
| 6,161,848 A | 12/2000 | Beumer et al. | |
| 6,203,035 B1 | 3/2001 | Ondrasik | |
| D457,239 S | 5/2002 | Kunlk | |
| 6,382,434 B1 | 5/2002 | Silberg | |
| 6,749,208 B2 * | 6/2004 | Orozco ................ | A47F 5/137 211/126.1 |
| 6,749,308 B1 | 6/2004 | Niendort et al. | |
| 7,631,773 B1 | 12/2009 | Calabrisotto et al. | |
| 8,152,181 B2 | 4/2012 | Tomlinson | |
| 8,196,874 B2 * | 6/2012 | Zitting ................ | A61M 5/1415 211/126.7 |
| 8,657,241 B2 * | 2/2014 | Zitting ................ | A61M 5/1415 211/194 |
| 9,227,007 B2 * | 1/2016 | Zitting ................ | A61M 5/1415 |
| 2002/0096608 A1 | 7/2002 | Cedarberg, III | |
| 2003/0196975 A1 | 10/2003 | Murray et al. | |
| 2006/0196997 A1 | 9/2006 | Johnson | |
| 2007/0063460 A1 | 3/2007 | O'Quin | |
| 2007/0187559 A1 | 8/2007 | Newkirk et al. | |
| 2007/0205339 A1 | 9/2007 | Anthes et al. | |
| 2008/0156946 A1 | 7/2008 | Schmutzer et al. | |
| 2009/0321589 A1* | 12/2009 | Hampton ............ | A61M 5/1415 248/121 |

FOREIGN PATENT DOCUMENTS

| | | | |
|---|---|---|---|
| DE | 202 19 431 | 4/2003 | |
| EP | 1 882 485 | 1/2008 | |
| GB | 2481649 A * | 1/2012 | ............. A61M 5/14 |
| JP | H07-15025 | 4/1995 | |
| JP | 2001 129057 A | 5/2001 | |
| JP | 2003310712 | 11/2003 | |
| JP | 2004049491 | 2/2004 | |
| JP | 3755754 | 3/2006 | |
| WO | 2007/056830 | 5/2007 | |

\* cited by examiner

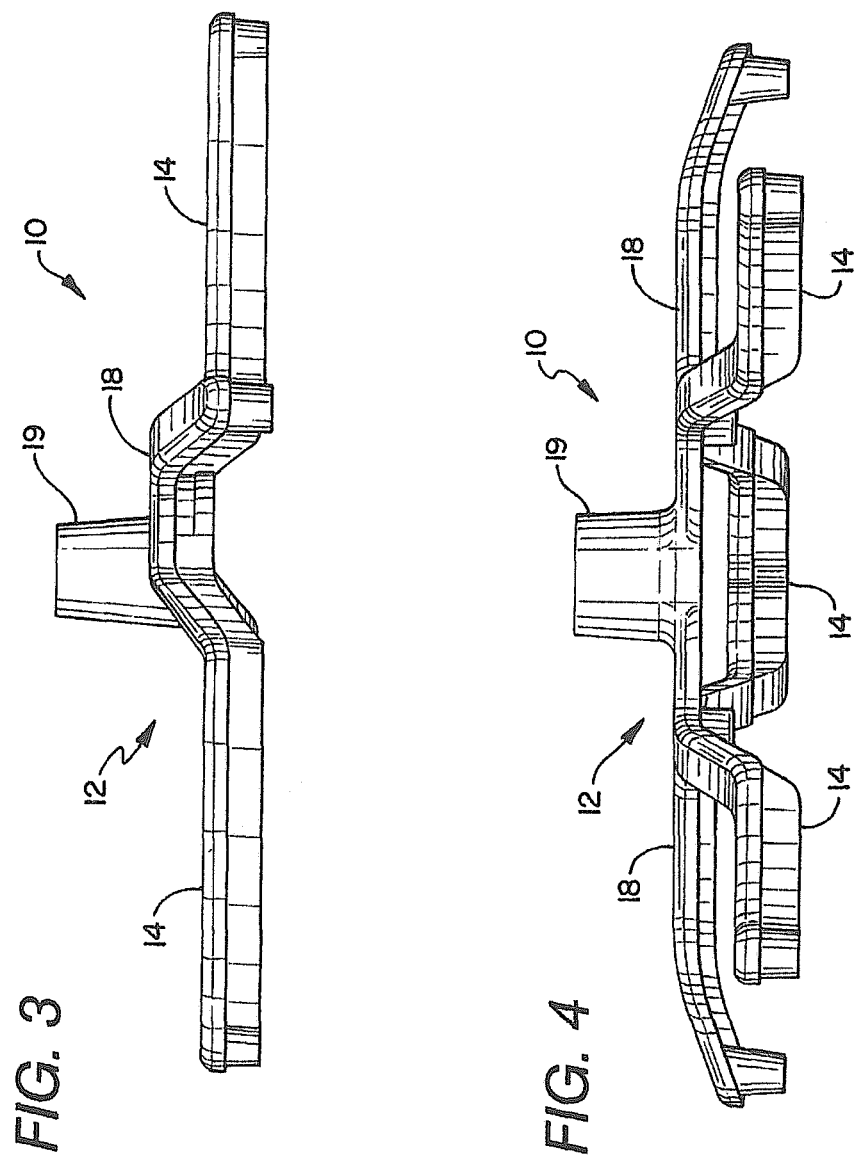

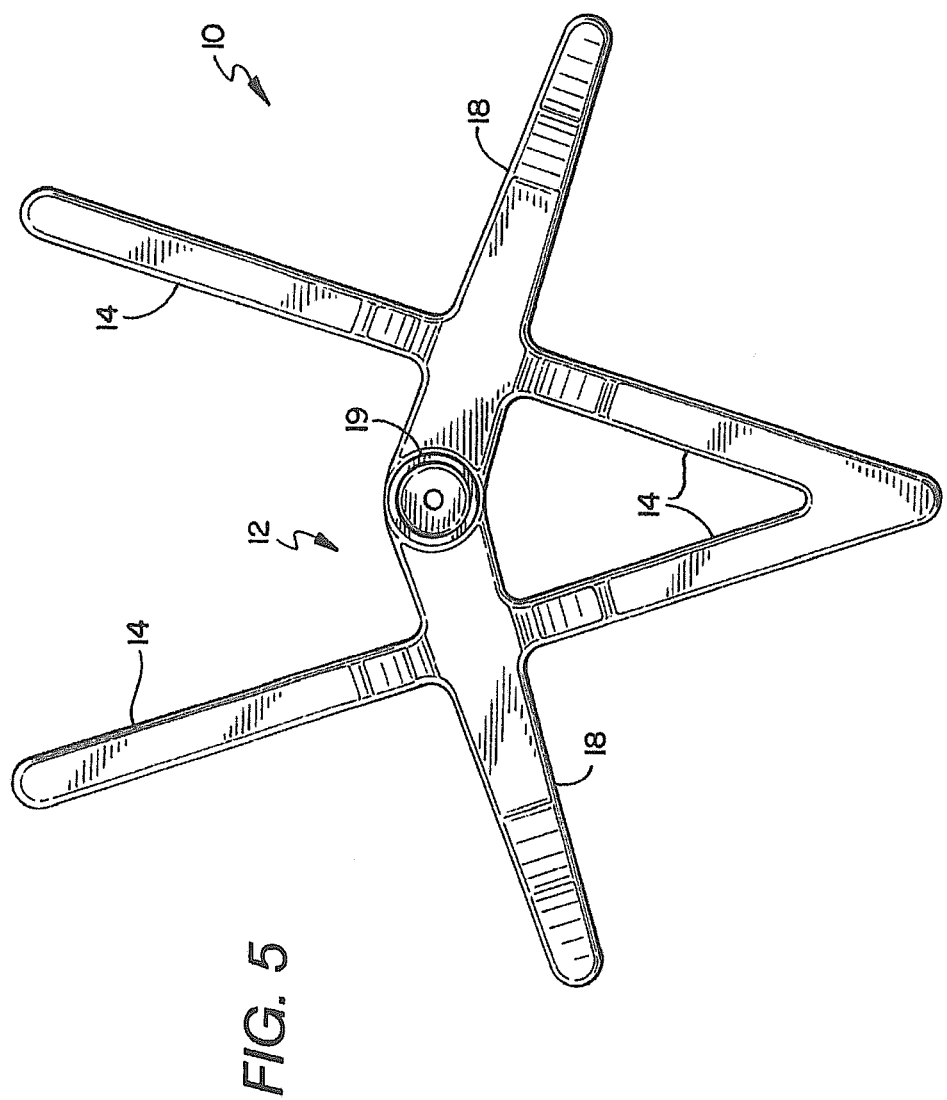

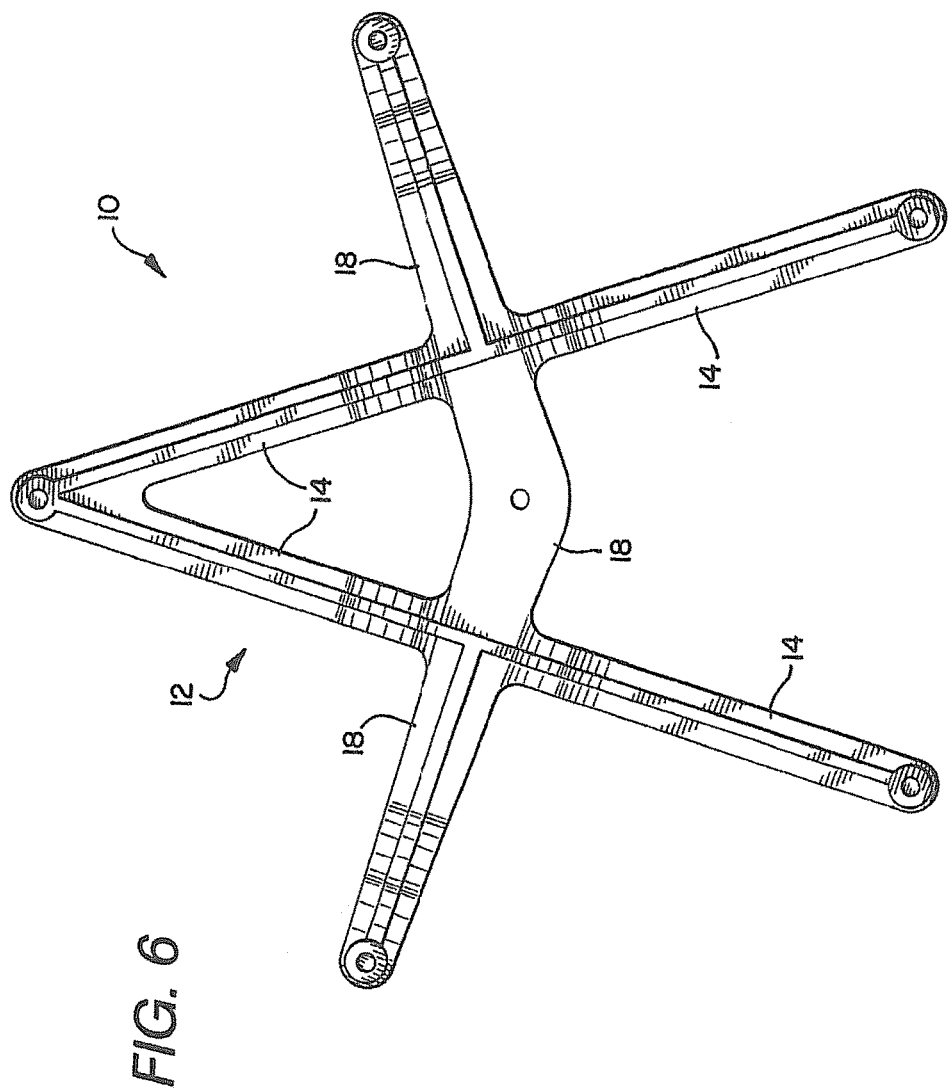

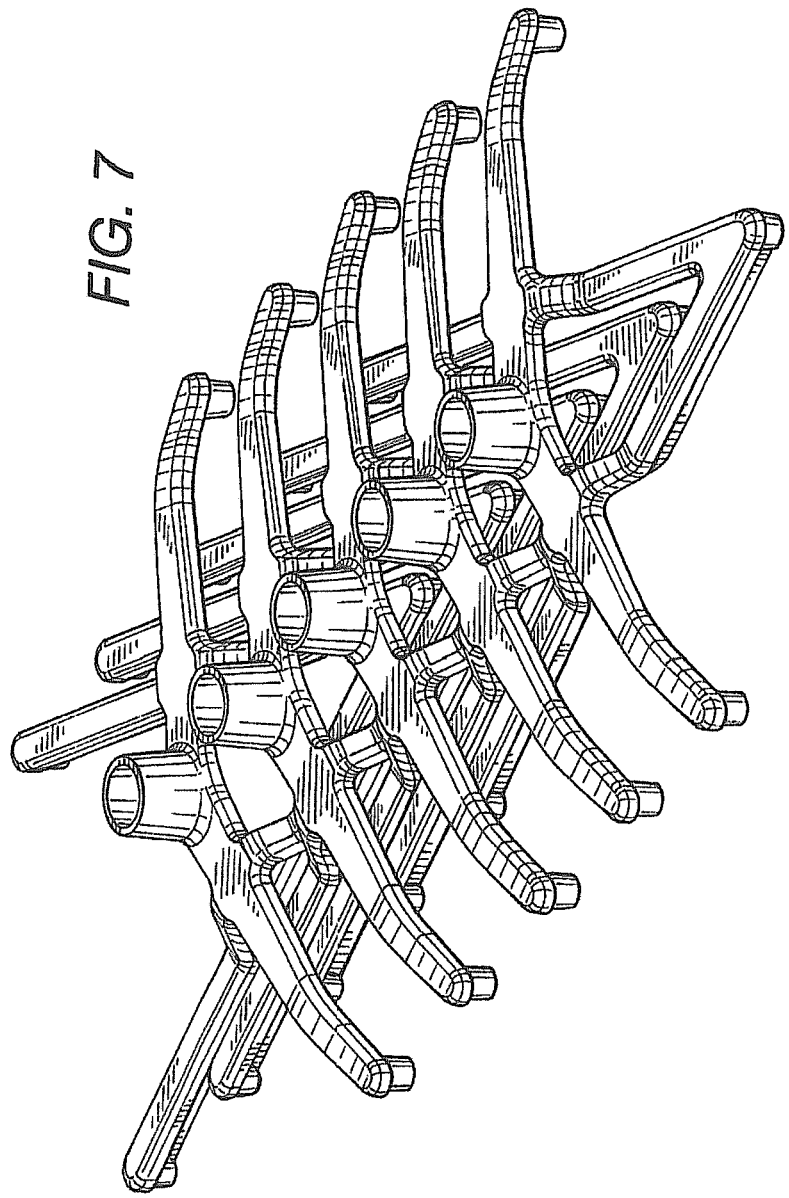

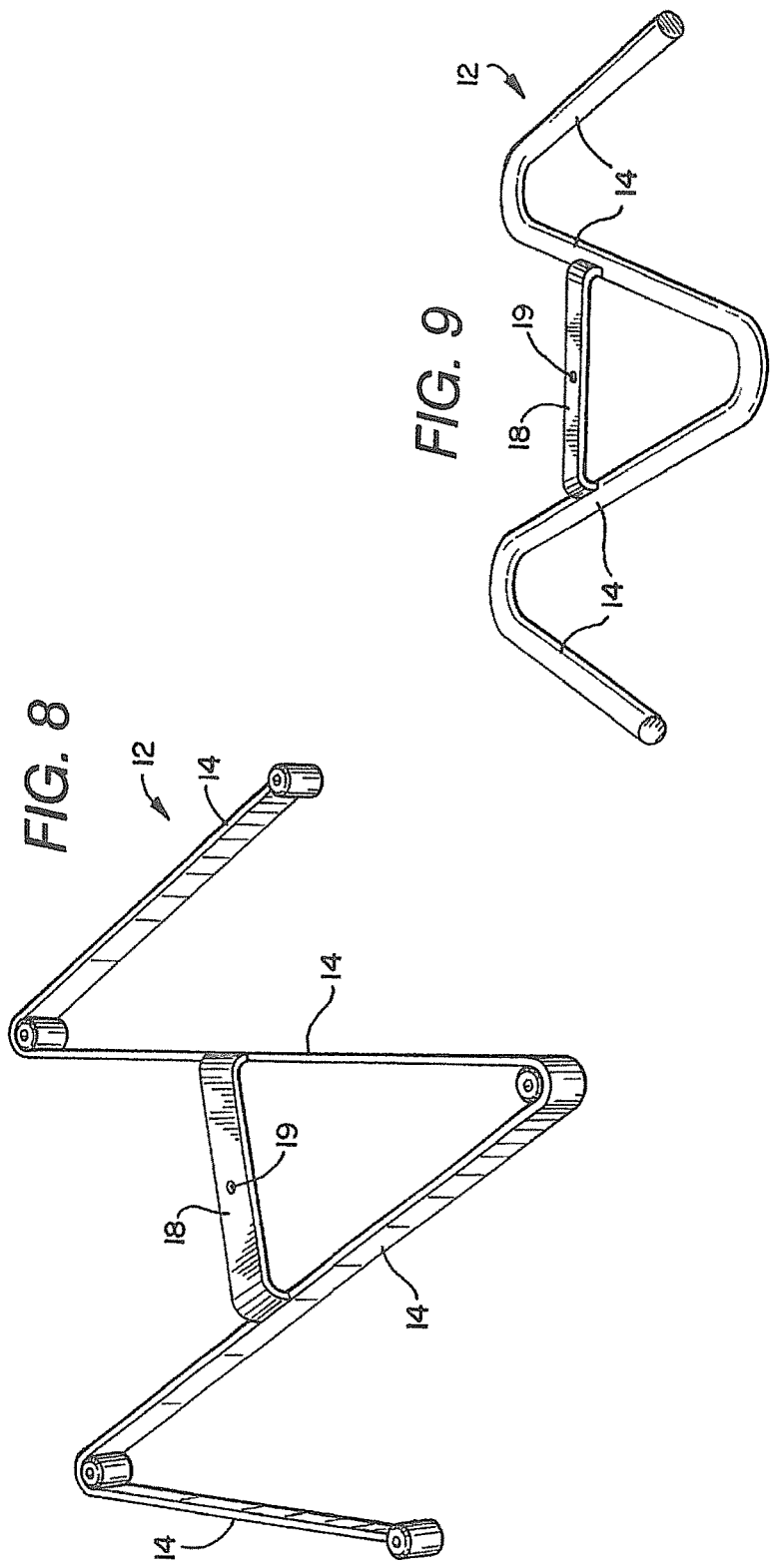

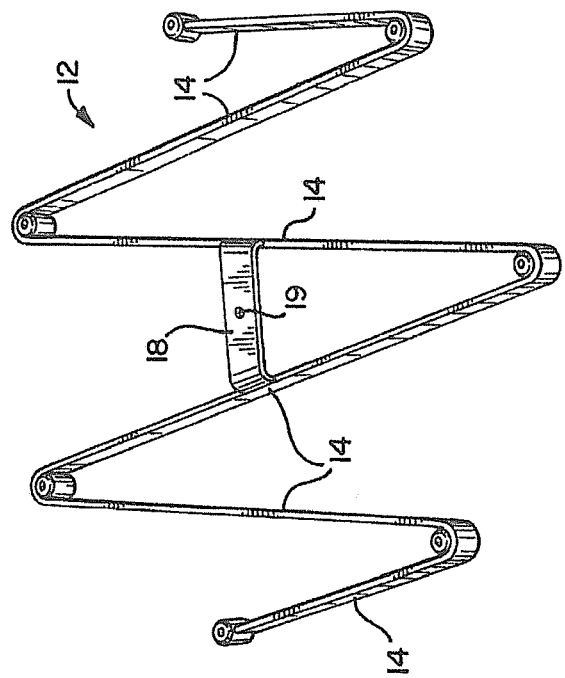
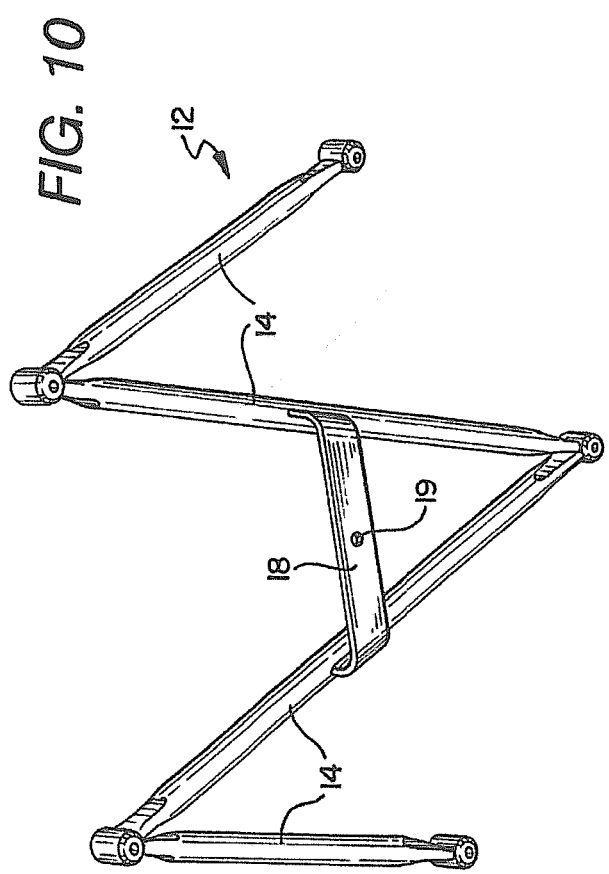

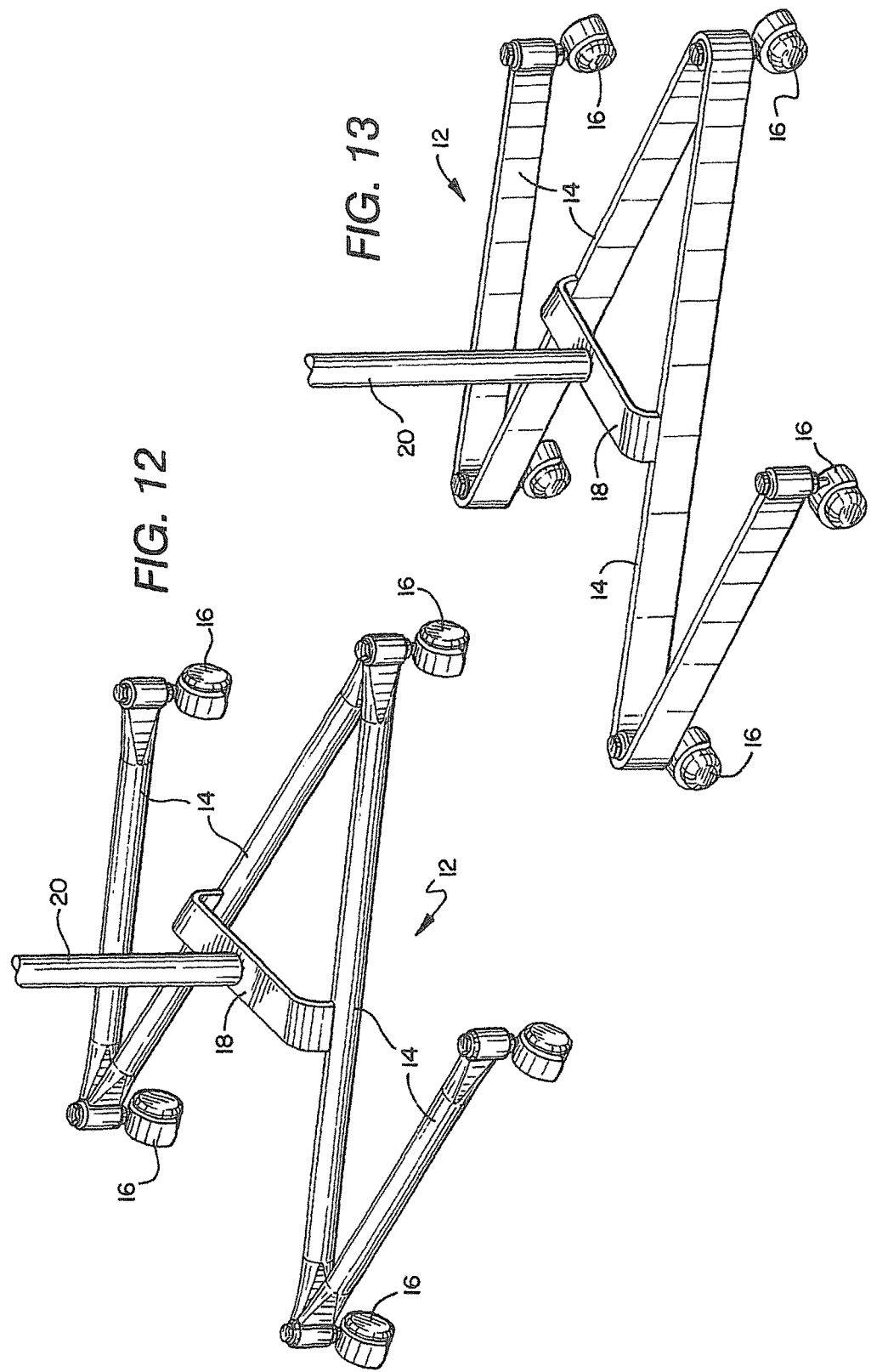

STORABLE INTRAVENOUS STANDS

RELATED APPLICATIONS

The present application is a continuation of U.S. patent application Ser. No. 14/187,943 filed Feb. 24, 2014, which is a divisional of U.S. patent application Ser. No. 13/469,863 filed May 11, 2012, which is a divisional of U.S. patent application Ser. No. 12/287,535 filed Oct. 10, 2008, which claims priority to U.S. Provisional Patent Application Ser. No. 60/998,863 filed Oct. 12, 2007, entitled Storable Intravenous Stands; and the contents of all of which are incorporated by reference herein.

TECHNICAL FIELD

The present invention is directed to stands for intravenous (IV) units, and more particularly to stands capable of being stored in such a manner so as to reduce the amount of space required during storage.

BACKGROUND OF THE INVENTION

There are many styles of portable intravenous stands available today. In general, the intravenous stand includes a base support having a set of wheels or the like and a bar extending upward from the base, wherein the intravenous delivery unit is suspended from the bar and is capable of accompanying the user during movement. The intravenous stand is preferably designed such that it is resistant to tipping over. In most cases, such a design includes a sufficiently broad base support. Unfortunately, unless the broad base support is capable of being collapsed, storage of the intravenous stands requires a substantial amount of floor space. Alternatively, the intravenous stands may be stacked upon each other during storage, however it would be preferable if lifting the stand was not required.

The present invention is directed to addressing these and other matters.

SUMMARY OF THE INVENTION

The present invention is directed to an intravenous stand including a base support that facilitates storage of multiple intravenous stands within close proximity to each other.

In one embodiment of the present invention, the portable intravenous stand includes a base member having a plurality of segments that substantially lie within a first plane, and a plurality of rotating members operatively connected—e.g., bolted, welded, press-fit, snap-fit, and any other attachment mechanism known to one of ordinary skill in the art that is used to connect such cooperating components—to the base member. An outrigger member is connected between two adjacent segments of the base member, wherein the outrigger member includes a portion thereof being higher than a portion of the plurality of segments, which facilitates the positioning of another similarly configured portable intravenous stand proximate thereto and under the outrigger member. Preferably, a support is integral to the outrigger member and capable of maintaining a pole member substantially perpendicular to the first plane.

In another embodiment of the present invention, the portable intravenous stand comprises a base member including a plurality of segments substantially lying within a first plane, wherein the plurality of segments further include a main segment having a first and second end and preferably extending through the stand's center of mass; a first adjacent segment having a first and second end, wherein the first end of the first adjacent segment being operatively connected to the first end of the main segment; a first rotating member being operatively attached to the base member proximate the connection of the main segment and the first adjacent segment; a second adjacent segment having a first and second end, wherein the first end of the second adjacent segment being operatively connected to the second end of the main segment; a second rotating member being operatively attached to the base member proximate the connection of the main segment and the second adjacent segment; a third rotating member being operatively attached to the base member proximate the second of the first adjacent segment; a fourth rotating member being operatively attached to the base member proximate the second end of the second adjacent member; a pair of concentric circles lying within the first plane, wherein the first and second rotating members lying upon a circumference of a first circle and the third and fourth rotating members lying upon a circumference of a second circle; and, a support integral to the base member and capable of maintaining a pole member substantially perpendicular to the first plane.

Alternatively, the embodiment further comprises a third adjacent segment having a first and second end, wherein the first end of the third adjacent segment being operatively connected to the second end of the first adjacent segment; a fifth rotating member being operatively attached to the base member proximate the second end of the third adjacent segment; a fourth adjacent segment having a first and second end, wherein the first end of the fourth adjacent segment being operatively connected to the second end of the second adjacent segment; and, a sixth rotating member being operatively attached to the base member proximate the second end of the fourth adjacent segment; a third concentric circle lying within the first plane wherein the fifth and sixth rotating member essentially lie upon the circumference of the third circle.

In an alternate embodiment of the present invention, the concentric circles have the same circumference such that the first, second, third, fourth, and any additional rotating members essentially lie upon the same circle and are preferably spaced about the circumference an equal distance apart from each other.

In another embodiment, a portable intravenous stand comprises a base member including a plurality of segments, wherein the plurality of segments further comprise a first segment having a first end and a second end; a second segment having a first end and a second end wherein the first end of the second segment is operatively attached to the first end of the first segment forming a first junction lying within a first plane; an outrigger member having a first end and a second end wherein the outrigger member first end is operatively attached to the first junction; a first rotating member operatively attached proximate the second end of the first segment; a second rotating member operatively attached proximate the second end of the second segment; a third rotating member operatively attached proximate the second end of the outrigger member wherein the first, second and third rotating members are within a second plane parallel to and lower than the first plane; a circle lying within the second plane, wherein the first, second and third rotating members essentially lie upon a circumference of the circle; and a support integral to the base member and capable of maintaining a pole member substantially perpendicular to the first plane.

It is an object of the present invention to provide a sturdy and sufficiently stable portable intravenous stand that includes a base capable of cooperating with bases of other similarly constructed portable intravenous stands such that the area required to store the portable intravenous stands is significantly less than those portable intravenous stands used today.

These and other aspects and attributes of the present invention will be discussed with reference to the following drawings and accompanying specification and claims.

BRIEF DESCRIPTION OF THE DRAWINGS

Having thus generally described the nature of the present invention, reference will now be made to the accompanying drawings showing, by way of illustration, preferred embodiments in which:

FIG. 3 is a right perspective view of the present invention shown in FIG. 1;

FIG. 4 is a rear perspective view of the present invention shown in FIG. 1;

FIG. 5 is a top perspective view of the present invention shown in FIG. 1;

FIG. 6 is a bottom perspective view of the present invention shown in FIG. 1;

FIG. 7 is a perspective view of several embodiments of the present invention shown in FIG. 1 as stored;

FIG. 8 is a perspective view of an alternative embodiment of the present invention;

FIG. 9 is a perspective view of another alternative embodiment of the present invention;

FIG. 10 is a perspective view of another alternative embodiment of the present invention;

FIG. 11 is a perspective view of another alternative embodiment of the present invention;

FIGS. 12-14 are perspective views of various embodiments of the present invention show with the pole member attached thereto;

FIG. 19A-19C depict an alternate embodiment of the base member of the portable intravenous stand of the present invention, wherein FIG. 19A is an elevated view thereof, FIG. 19B is a plan view thereof, and FIG. 19C shows multiple stands in storage;

FIG. 20A-20C depict an alternate embodiment of the base member of the portable intravenous stand of the present invention, wherein FIG. 20A is a plan view thereof, FIG. 20B is an elevated view thereof, and FIG. 20C shows multiple stands in storage;

DETAILED DESCRIPTION OF THE PRESENT INVENTION

Figure 1:
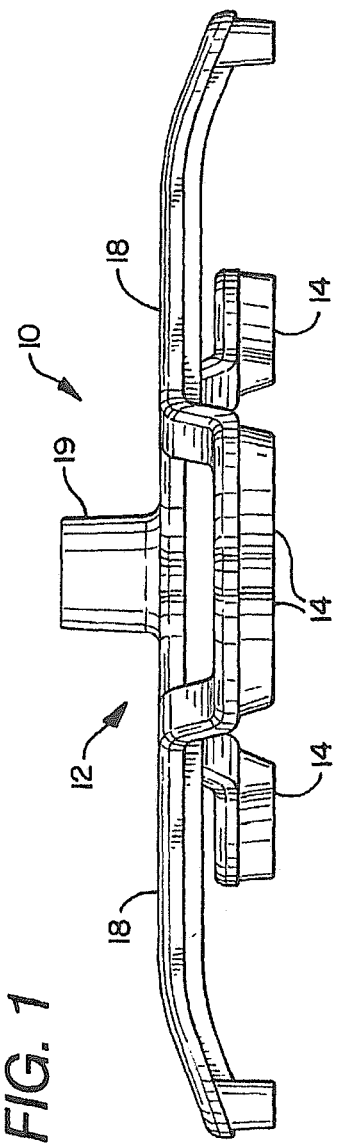
FIG. 1 is a front perspective view of the preferred embodiment of the present invention.
Figure 2:
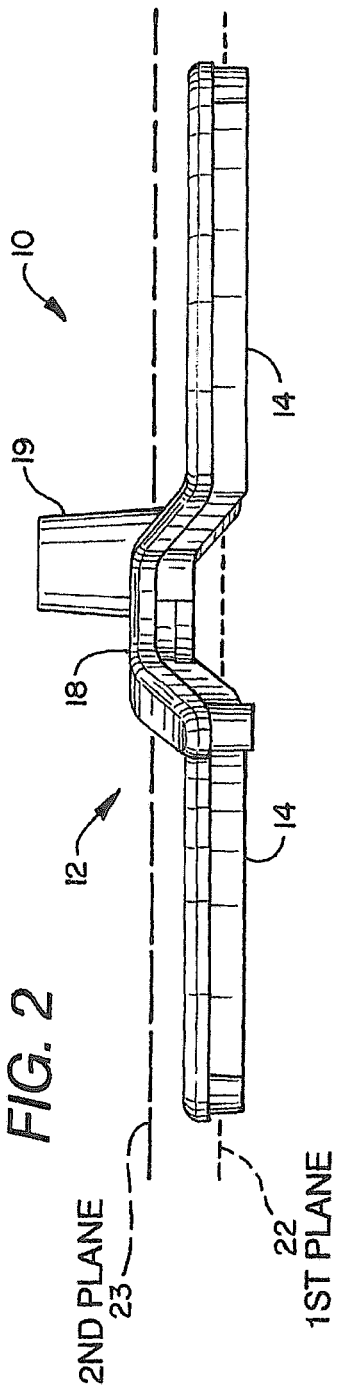
FIG. 2 is a left perspective view of the present invention shown in FIG. 1.
Figure 14:
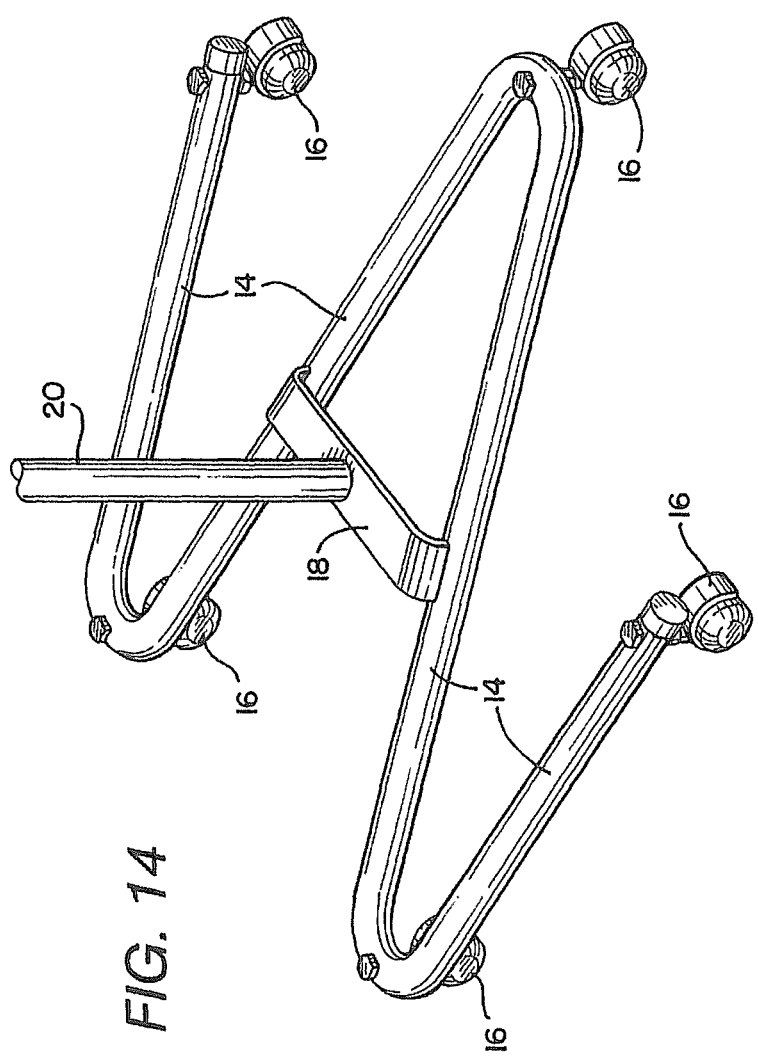
Figure 15:
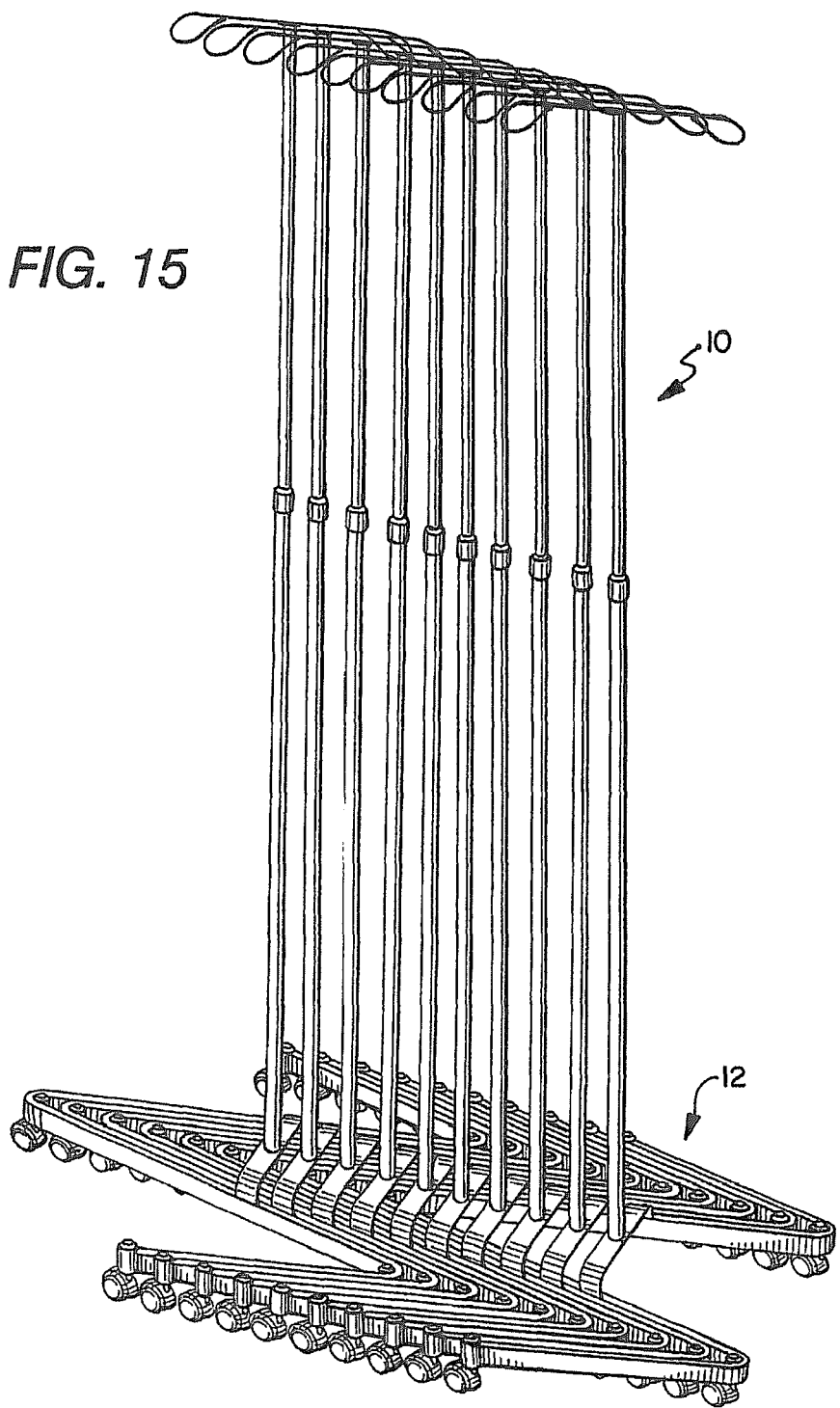
FIGS. 15-18 are perspective views of various embodiments of the portable intravenous stands of the present invention and attaching pole members as stored.
Figure 16:
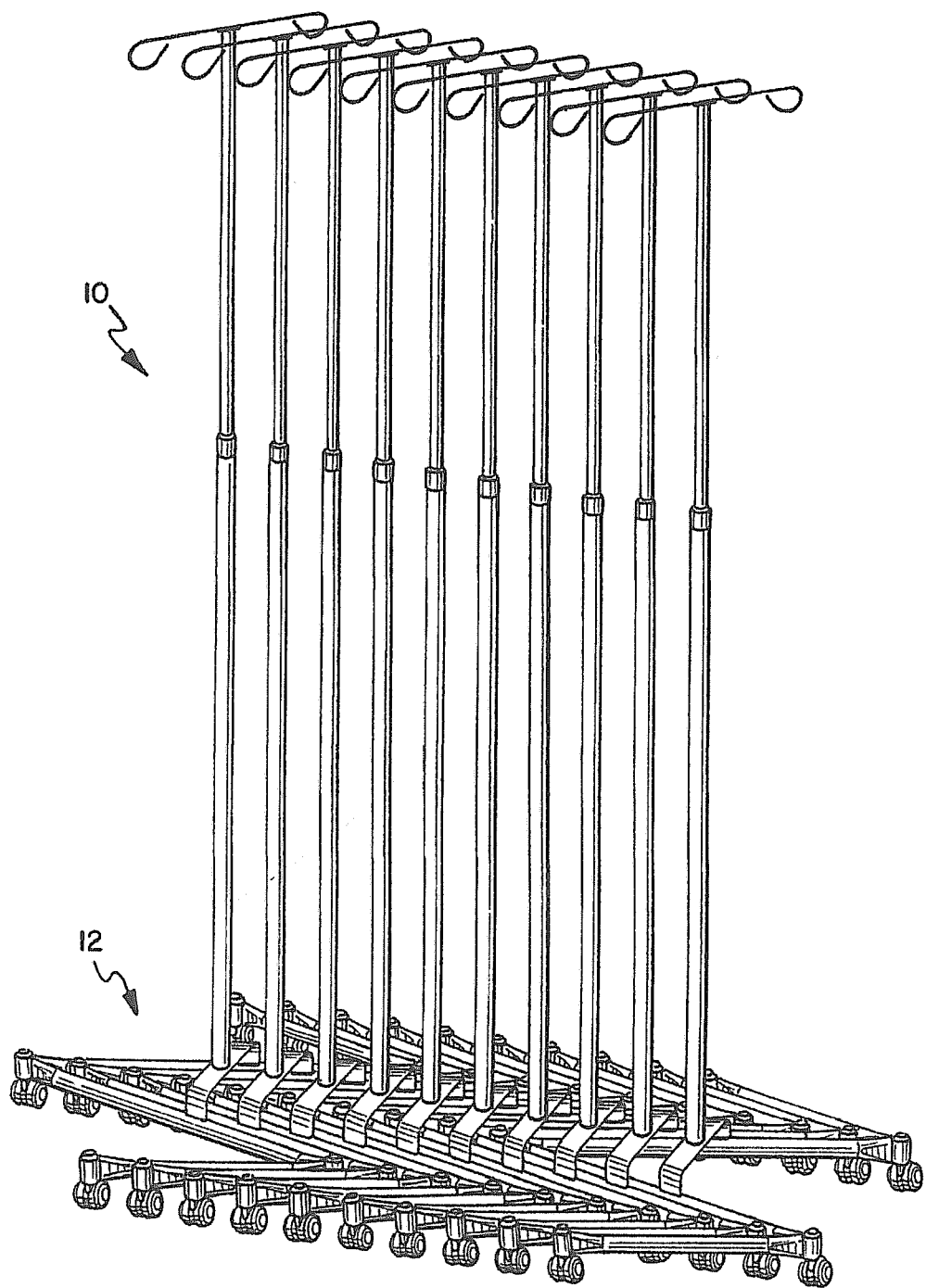
Figure 17:
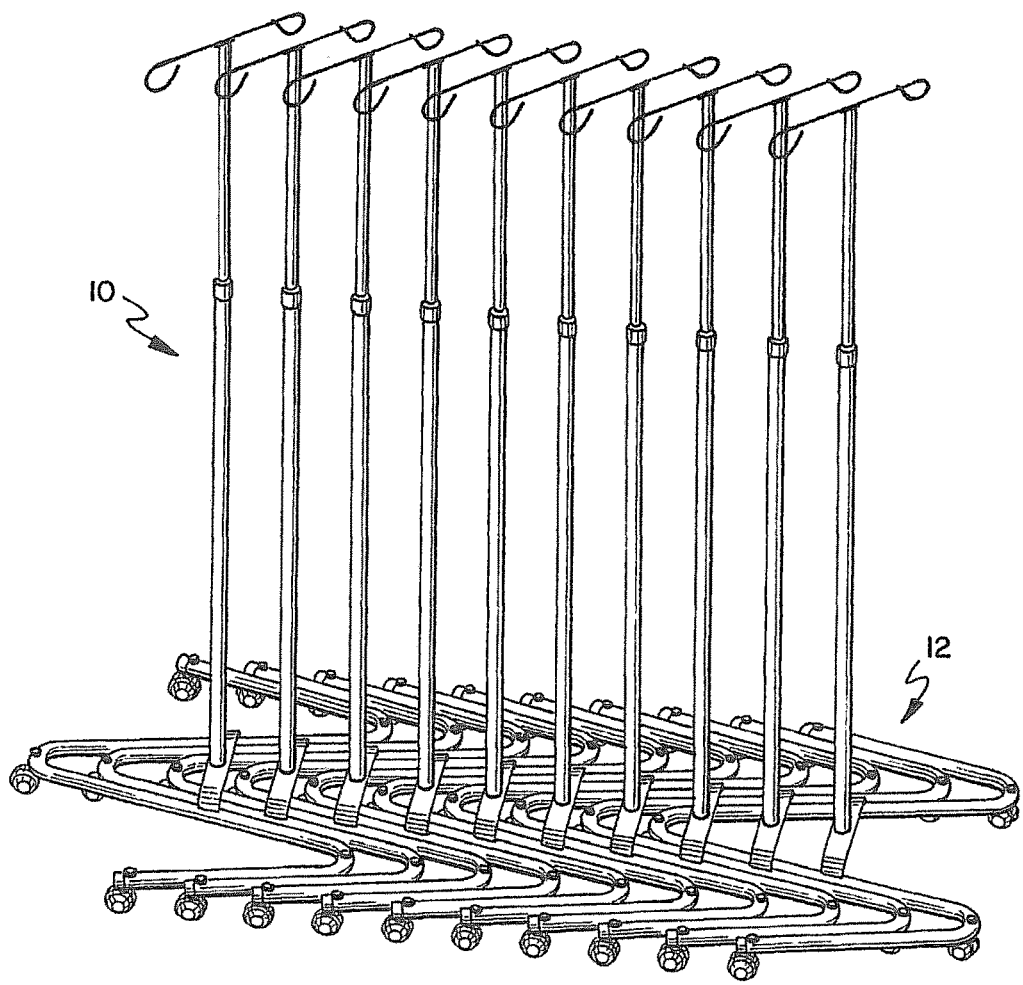
Figure 18:
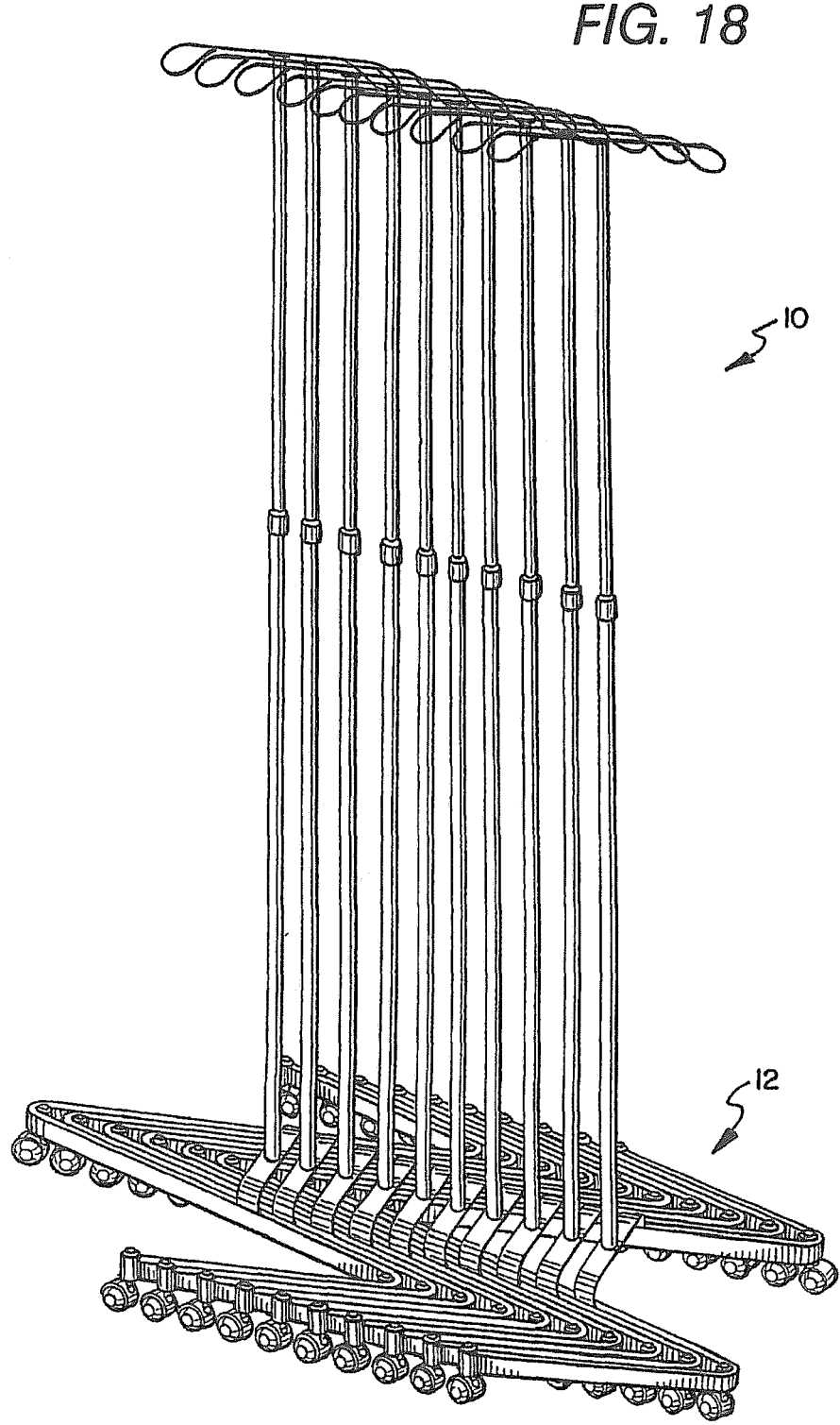
Figure 19A:
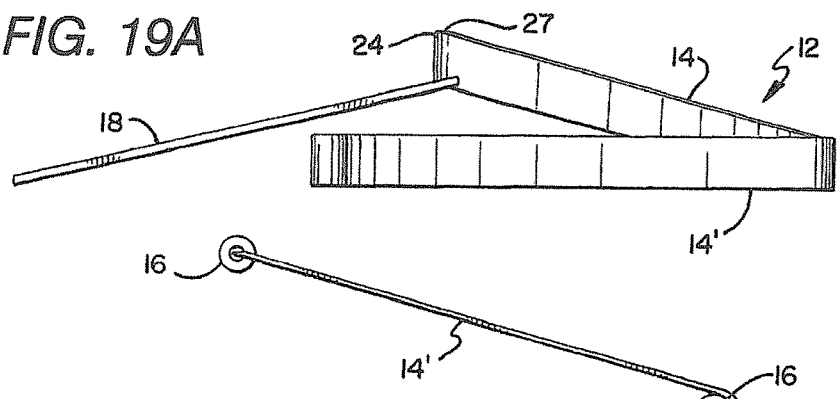
Figure 19B:
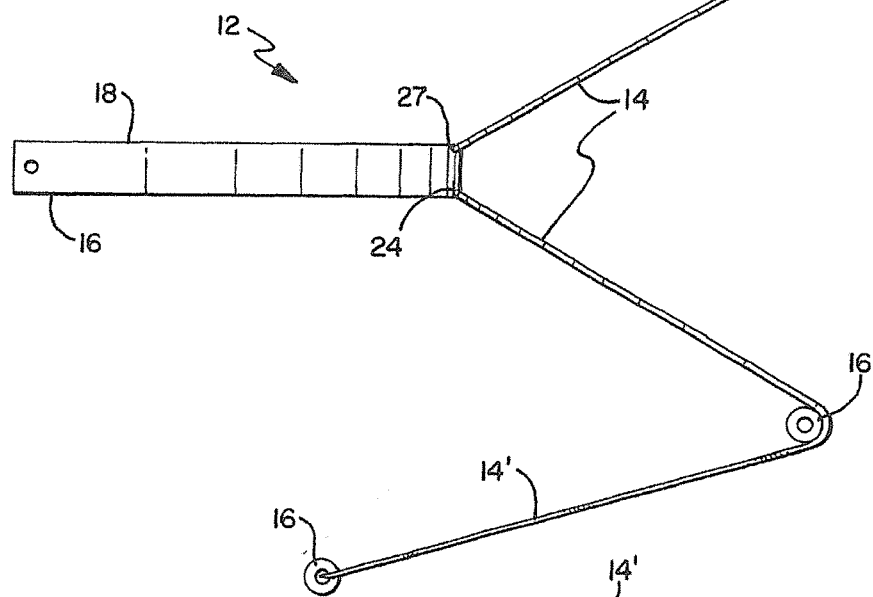
Figure 19C:
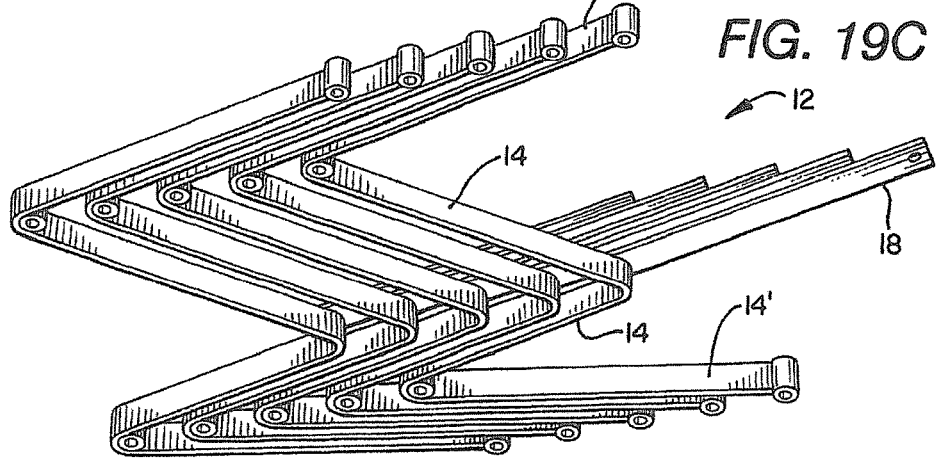
Figure 20A:
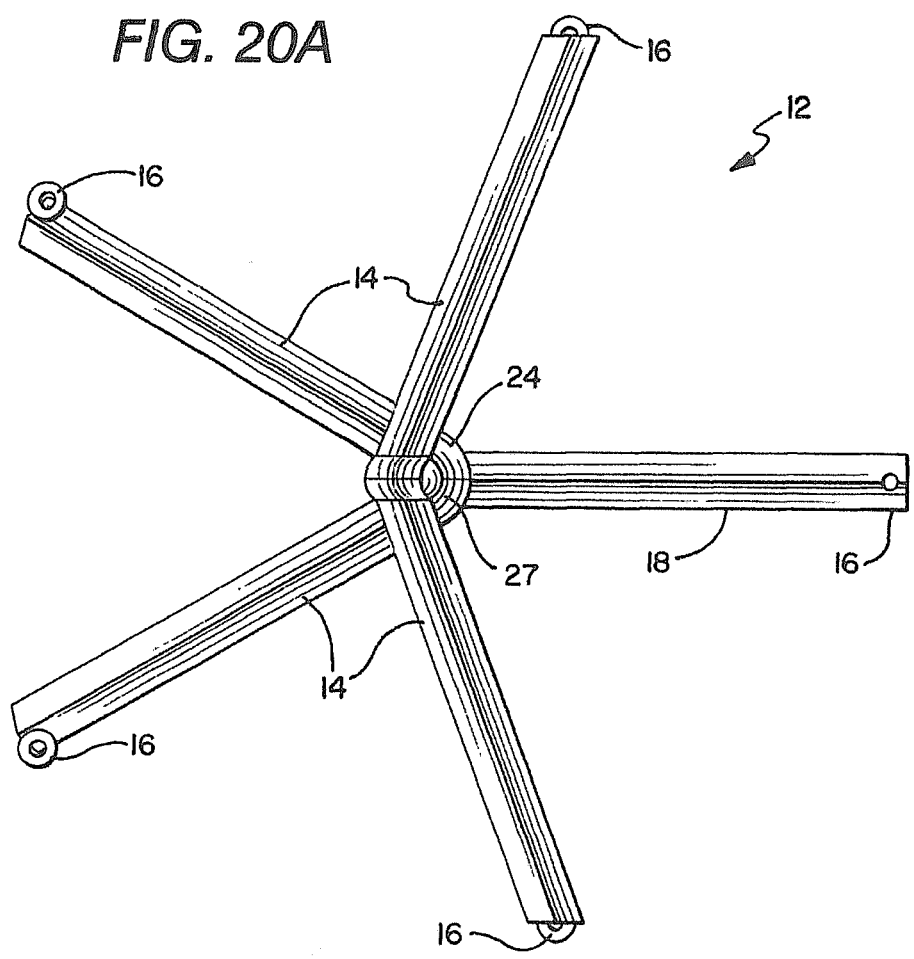
Figure 20B:
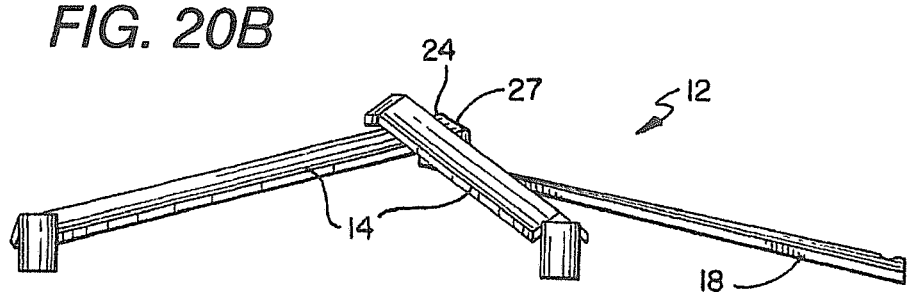
Figure 20C:
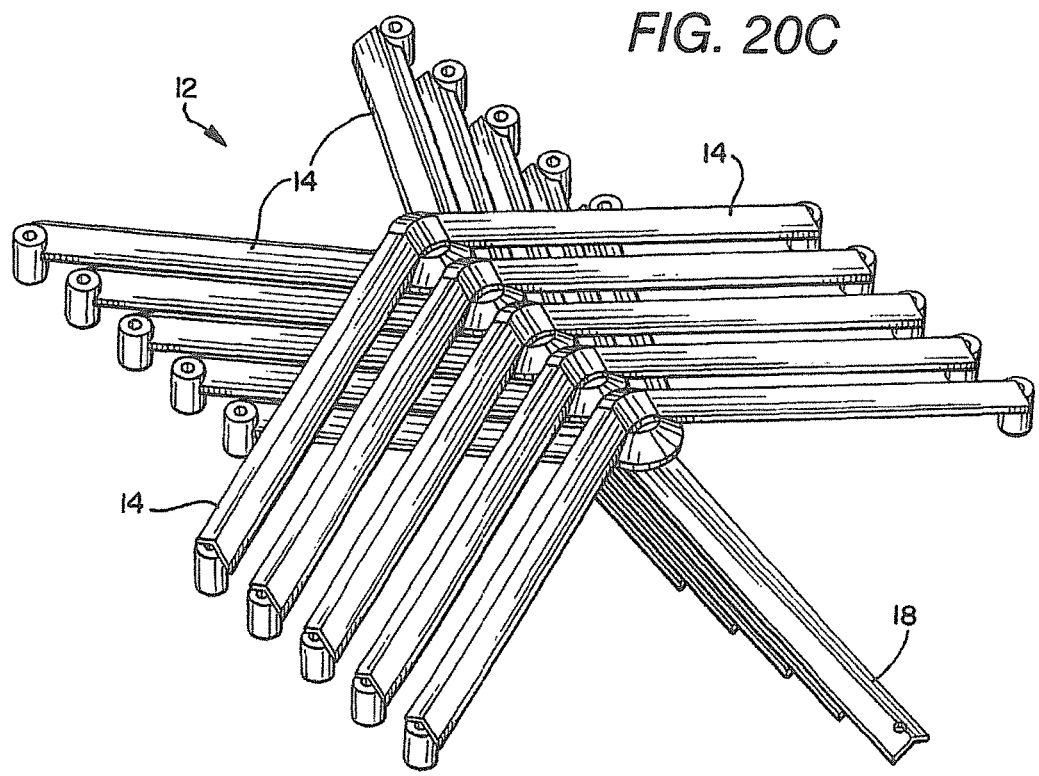

While the present invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

The preferred embodiment of the present invention is shown in FIGS. 1-7, wherein various views depict a portable intravenous stand 10 having a base member 12 further including a plurality of segments 14. The plurality of segments 14 lies substantially within a plane 22 (which is substantially parallel with the paper with respect to FIGS. 5 and 6). A plurality of rotating members 16 (not shown in FIGS. 1-7) can be operatively connected to the base member 12, preferably proximate the end(s) of each segment. It is to be understood that the operative connection of any part/component of the portable intravenous stand 10 contemplates utilizing any connecting mechanism known to one of ordinary skill in the art for connecting such cooperating components, such as, and not limited to: welds, bolts, screws, hinges, pivots, snaps, fittings, crimps, and alike. An outrigger member 18 is connected between two adjacent segments 14 of the base member 12, and preferably extends past the adjacent segments to provide additional stability to the stand 10. Similar to the segments 18, a rotating member 16 can be attached proximate each end of the outrigger member 18. The outrigger member 18 is configured such that its end, when attached to rotating members 16 would lie on the circle and equidistant apart from the other rotating members. The outrigger member 18 includes at least a portion thereof—and preferably a substantial portion thereof—that does not lie within the same plane as the plurality of segments 14; that is, at least a portion of the outrigger member 18 lies in another plane 23 that is above or higher than the first plane 22 and which is preferably substantially parallel to the first plane. The higher portion of the outrigger member 18 facilitates the positioning of another similarly designed portable intravenous stand 10 there under and proximate thereto. See FIG. 7. A support 19 is preferably integral to the base member 12 and is capable of maintaining a pole member 20 substantially perpendicular to the planes 22, 23 respectively containing the plurality of segments 14 and the outrigger member 18.

As shown in all the figures, the present invention contemplates utilizing various amounts and varieties of segments 14, outrigger members 18, and rotating members 16. That is, the base member 12 can include two or more segments 14 of flat or rounded stock made of metal, non-metal, plastic, polymer, rubber, composite, solid, non-solid, and combinations thereof. See FIGS. 8-14. The preferred embodiment of the present invention shown in FIGS. 1-7 is cast out of aluminum and powder-coated. The rotating members 16 can also be selected from among a variety of types know to those of ordinary skill in that art; including and not limited to wheels, casters, balls, and rollers.

In other embodiments of the present invention shown in FIGS. 19A-19C and 20A-20C, a base member 12 comprises an outrigger member 18, at least two adjacent segments 14, and an elevated junction 27 proximate the center of mass 24. The outrigger member 18, having a first end and a second end, extends from the base member 12 proximate its center of mass 24, but does not connect between, nor extend past, adjacent segments 14. The outrigger member 18 first end is connected to adjacent segments proximate the junction 27. At least a portion of the outrigger member 18 is elevated and perhaps inclined toward the elevated junction 27. The angle of incline can be approximately 15° but other incline angles would be acceptable. The incline is of adequate steepness to facilitate the passage of one outrigger member of one base member 12 under another base member of an adjacent similarly configured portable intravenous stand 10 such that the poles of the stands are in close proximity. A rotating member can be attached proximate the outrigger member 18 second end.

At least two adjacent segments 14, having first and second ends, extend from proximate junction 27. The first ends of adjacent segments 14 are attached to the outrigger member 18 first end proximate junction 27. At least a portion of the adjacent segments 14 is elevated and perhaps inclined toward the elevated junction 27. The angle of inclination can be similar to the incline of outrigger member 18. Rotating members can be attached proximate the adjacent segment second ends.

The junction 27 is elevated above the outrigger member 18 and adjacent segments 14 second ends such that the center of mass is in a first plane and the second ends are in a second plane parallel to the first plane. The elevated junction 27 facilitates the passage of outrigger member 18 of another similarly configured portable intravenous stand 10 under the junction 27 and positioning of the stands 10 in close proximity. See FIGS. 19C and 20C. A support 19 is attached proximate junction 27. A rotating member, not shown, can be attached proximate each second end of outrigger member 18 and segments 14. Additional segments 14' can be attached proximate second ends of segments 14 to improve the stability of the base.

In all embodiments of the present invention including the outrigger member 18 extending between at least two segments 14 of the base member 12—e.g., FIGS. 1-18, 23, and 24—it is preferable that at least a portion of the outrigger member is raised above a portion of the plurality of segments such that during storage, a portion of the segment of an adjacent stand 10 is capable of passing under the outrigger member to facilitate close positioning of the stands as shown in FIGS. 7 and 15-18. While the outrigger member 18 has been shown extending between two adjacent segments 14 closest to the center of the base member 12, it is to be understood that the outrigger member can extend past the segments (as shown in FIGS. 1-7) and/or be attached to other segments as well. Additional discrete outrigger members 18 can also be utilized to branch between subsequent adjacent segments 14 to provide increased sturdiness to the base member 10. The additional outrigger members 18 preferably also include at least a portion raised above a portion of the plurality of segments 14, which facilitates close positioning of additional stands during storage. The additional outrigger member 18 can be branched between at least any two segments 14—not necessarily immediately adjacent segments—and is not required to be aligned such that if extended further, it would eventually pass proximate to the base member's center. The present invention further contemplates that an additional support 19 can be attached or integral with the additional discrete outrigger member 18.

Figure 21:
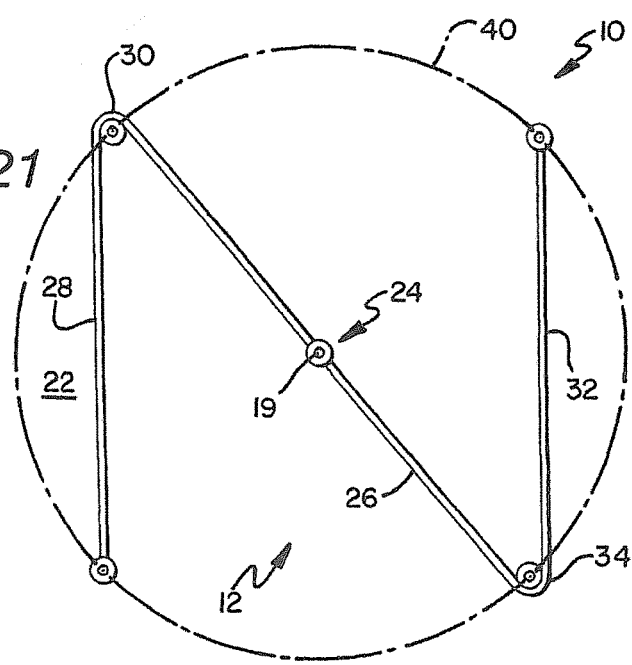
FIG. 21 is an alternate embodiment of the base member of the portable intravenous stand of the present invention.
Figure 22:
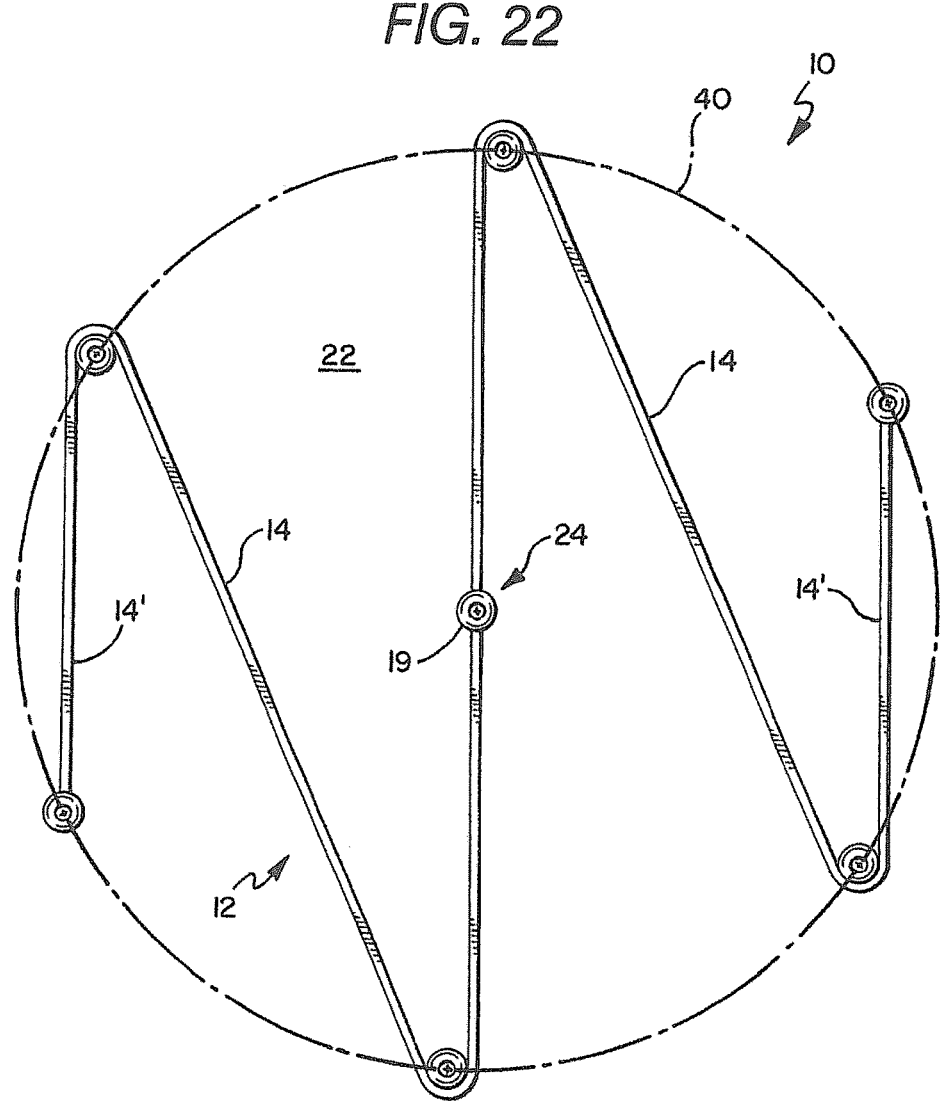
FIG. 22 is an alternate embodiment of the base member of the portable intravenous stand of the present invention.

In yet another embodiment of the present invention shown in FIGS. 21 and 22, the portable intravenous stand 10 includes a base member 12 having a center of mass 24 and lying substantially within a plane 22 (substantially parallel with the paper). The base member 12 includes a main segment 26 that preferably extends through or proximate the base member's 12 center of mass 24. A first adjacent segment 28 having a first and second end is attached to a first end 30 of the main segment, and a second adjacent segment 32 having a first and second end is attached to a second end 34 of the main segment 26 forming a Z-shaped base 12. An angle α between the main segment 26 and first adjacent segment 28 and second adjacent segment 32 is formed at the points of attachment. The angle α can be approximately 15° to 75°. A first rotating member (not shown in FIGS. 21 and 22) can be attached proximate the attachment of the main segment 26 and the first adjacent segment 28, and a second rotating member (not shown in FIGS. 21 and 22) can be attached proximate the attachment location of the main segment 26 and the second adjacent segment 32. Additional segments 14' can be attached proximate the second end of adjacent segments 14 forming a base member 12 having a zig-zag form. The additional segments 14' increase the stability of the stand. Rotating members can be attached to the free ends of the segments 14'. A pole member 20 (not shown in FIGS. 21 and 22) can extend substantially vertical from the support 19 that is preferably integral with the base member 12 and proximate the center of mass 24, such that the base member enables the close positioning of corresponding segments of other similarly designed portable intravenous stands. An additional rotating member 16 can be attached to the main segment 26 of the base member 12 and proximate its center of mass 24 and/or support 19.

Figure 23:
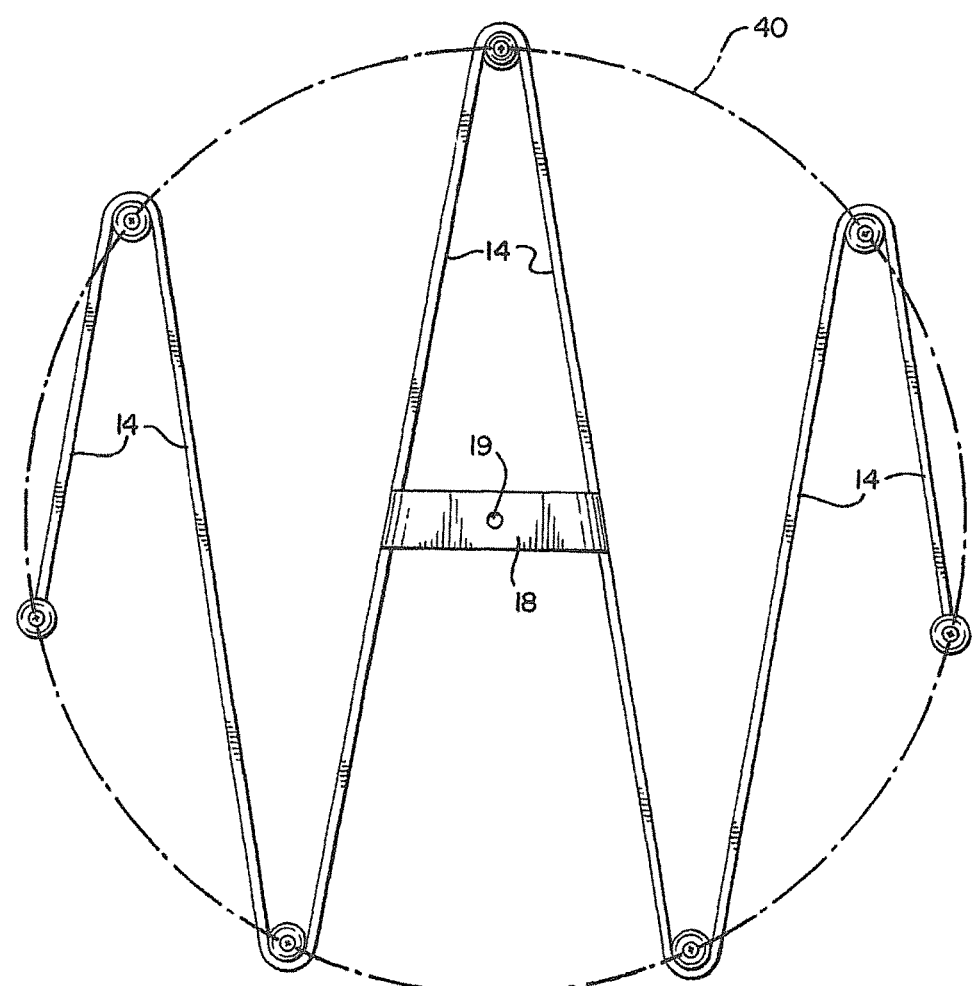
FIG. 23 is an alternate embodiment of the base member of the portable intravenous stand of the present invention.
Figure 24:
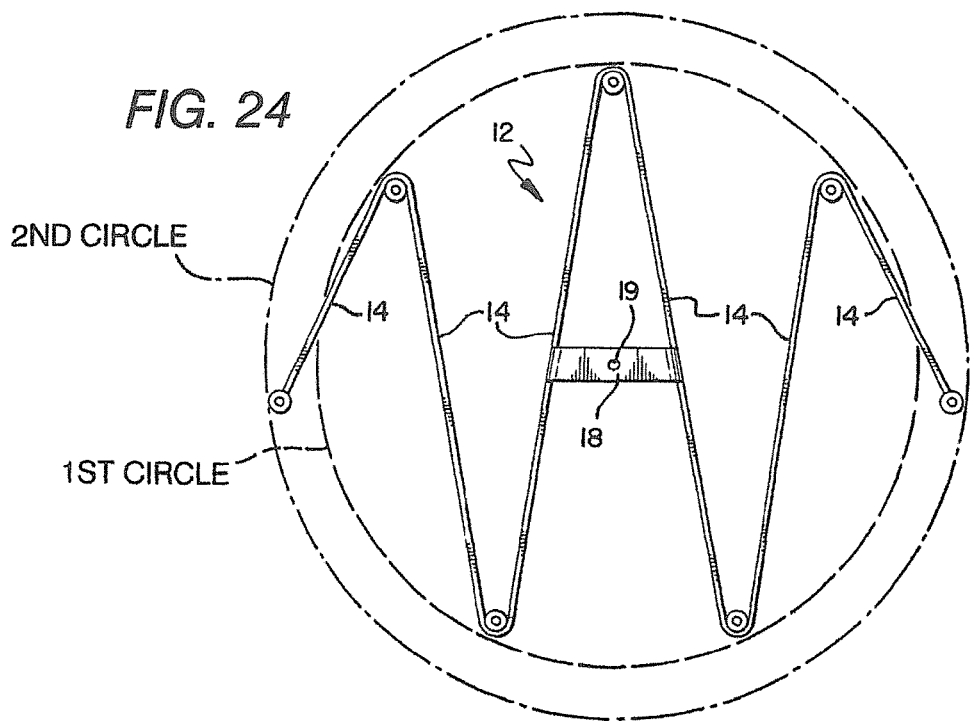
FIG. 24 is an alternate embodiment of the base member of the portable intravenous stand of the present invention; and, FIG. 25 is an alternate embodiment of the base member of the portable intravenous stand of the present invention.

As shown in FIGS. 21-23—and which is also applicable to the various embodiments of the present invention shown throughout the figures—a pair of rotating members can be attached to the base member 12, wherein the pair of rotating members lie upon a circumference of a circle 40 that lies parallel to the plane 22 wherein the circle's center is preferably aligned with the center of the support 19, which is preferably proximate to the stand's 10 center of mass 24. Additional rotating members can further be attached to the base member 12 and also located about the circumference 40 and preferably an equal distance apart from each other along the path of the circumference.

Referring back to FIGS. 1-7, the outrigger member 18 is configured such that the rotating members attached to its ends, which extend past the adjacent segments 14, lie on the circumference 40 along with the other rotating members, wherein the rotating members are preferable positioned an equal distance apart from each other along the path of the circumference. In FIGS. 1-7, one half of the outrigger member is substantially perpendicular to one of the adjacent segments and the other half of the outrigger member is substantially perpendicular to the other of the adjacent segments. The equidistant spacing of rotating members 16 about the circumference 40 provides substantial stability to the base member.

Figure 25:
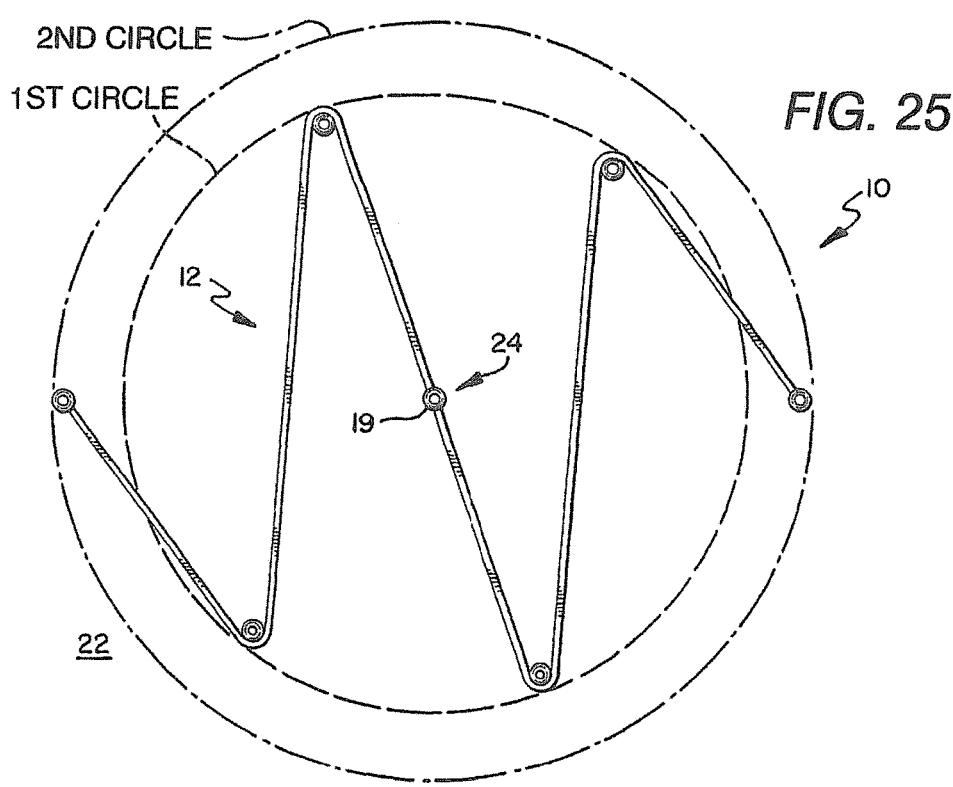

It is to be noted however that not all rotating members 16 need to be located proximate the circumference 40, but rather can be spaced a different distance from the support 19. In other words, other rotating members, preferably in pairs, can be positioned about another circle having a different circumference that is concentric with the first circumference 40 about the support 19, or the center of mass 24 of the stand 10; but where the concentric circumferences have different diameters (see FIGS. 24 and 25).

It is to be understood that additional embodiments of the present invention described herein may be contemplated by one of ordinary skill in the art and the scope of the present invention is not limited to the embodiments disclosed. While specific embodiments of the present invention have been illustrated and described, numerous modifications come to mind without significantly departing from the spirit of the invention, and the scope of protection is only limited by the scope of the accompanying claims.

What is claimed is:

1. A portable intravenous stand comprising:
a plurality of segments including a first segment and a second segment, the first segment and the second segment being angled with respect to one another so that a first end of the first segment is closer to a first end of the second segment than a second end of the first segment is to the second end of the second segment;
an outrigger member extending at least between the first segment and the second segment, wherein the first segment and the second segment each include an inclined portion proximate the outrigger member and the outrigger member includes at least a portion being elevated above the first segment and the second segment to facilitate positioning another similarly configured portable intravenous stand there under and proximate thereto; and,
a support integral to the outrigger member capable of maintaining a pole member substantially perpendicular to the outrigger member;
a plurality of rotating members, wherein at least one rotating member is operatively connected to at least one of the plurality of segments of the base member, wherein each of the plurality of rotating members are arranged upon a circle, wherein the circle lies within a plane that is located below the plurality of segments.

2. The portable intravenous stand of claim 1, wherein at least one rotating member is operatively connected to the outrigger member.

3. The portable intravenous stand of claim 1, wherein the plurality of rotating members being selected from the group consisting of a wheels, balls, rollers, and casters.

4. The portable intravenous stand of claim 1, wherein each of the plurality of rotating members are arranged upon the circle an equal distance apart from each other.

5. The portable intravenous stand of claim 4, wherein the support includes a longitudinal axis infinitely extending there from and intersecting a center of the circle.

6. The portable intravenous stand of claim 1, wherein the support includes a longitudinal axis which intersects a center of mass of the portable intravenous stand.

7. The portable intravenous stand of claim 1, wherein the plurality of rotating members is five or more.

8. A portable intravenous stand comprising:
a plurality of segments including a first segment and a second segment, the first segment and the second segment being angled with respect to one another so that a first end of the first segment is closer to a first end of the second segment than a second end of the first segment is to the second end of the second segment;
an outrigger member extending at least between at least two segments of the plurality of segments, wherein the outrigger member includes a portion being elevated above a portion of the plurality of segments to facilitate positioning another similarly configured portable intravenous stand there under and proximate thereto;
a support integral to the outrigger member and capable of maintaining a pole member; and,
a plurality of rotating members, at least one rotating member being operatively connected to at least one of the plurality of segments of the base member and the rotating members being disposed on a circle and the support being disposed at a center of the circle.

9. The portable intravenous stand of claim 8 wherein the pole member is maintained substantially perpendicular to the outrigger member.

10. The portable intravenous stand of claim 8 wherein the rotating members are located equidistant from each other on the circle.

11. The portable intravenous stand of claim 8 wherein the support includes a longitudinal axis infinitely extending there from and intersecting a center of mass of the portable intravenous stand.

12. The portable intravenous stand of claim 8 wherein the outrigger member extends beyond the at least two segments.

13. The portable intravenous stand of claim 8 wherein at least one rotating member is operatively connected to the outrigger member.

14. A portable intravenous stand comprising:
a plurality of segments including a first segment and a second segment, the first segment and the second segment being angled with respect to one another so that a first end of the first segment is closer to a first end of the second segment than a second end of the first segment is to the second end of the second segment;
the plurality of segments further including a third segment and a fourth segment each having a first end and a second end, wherein the first end of the third segment is connected to and extends from the second end of the first segment and the first end of the fourth segment is connected to and extends from the second end of the second segment;
an outrigger member extending at least between the first segment and the second segment, wherein the outrigger member includes at least a portion being elevated above the first segment and the second segment to facilitate positioning another similarly configured portable intravenous stand there under and proximate thereto; and,
a support integral to the outrigger member capable of maintaining a pole member substantially perpendicular to the outrigger member;
a plurality of rotating members, wherein at least one rotating member is operatively connected proximate each first end and second end of each of the first, second, third and fourth segments, wherein the plurality of rotating members are located on the circumference of a circle.

* * * * *